United States Patent
McCully et al.

(10) Patent No.: US 10,542,932 B2
(45) Date of Patent: Jan. 28, 2020

(54) SYSTEMS AND METHODS FOR MEASURING MITOCHONDRIAL CAPACITY

(71) Applicant: University of Georgia Research Foundation, Inc., Athens, GA (US)

(72) Inventors: Kevin K. McCully, Athens, GA (US); Terence E. Ryan, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 261 days.

(21) Appl. No.: 15/616,318

(22) Filed: Jun. 7, 2017

(65) Prior Publication Data
US 2017/0265804 A1 Sep. 21, 2017

Related U.S. Application Data

(62) Division of application No. 13/793,558, filed on Mar. 11, 2013, now Pat. No. 9,706,959.

(60) Provisional application No. 61/609,025, filed on Mar. 9, 2012.

(51) Int. Cl.
*A61B 5/1455* (2006.01)
*A61B 5/00* (2006.01)
*A61B 5/145* (2006.01)
*A61B 17/135* (2006.01)
*A61B 5/02* (2006.01)

(52) U.S. Cl.
CPC ........ *A61B 5/4866* (2013.01); *A61B 5/14546* (2013.01); *A61B 5/14551* (2013.01); *A61B 5/4519* (2013.01); *A61B 5/4884* (2013.01); *A61B 5/7225* (2013.01); *A61B 5/7278* (2013.01); *A61B 5/02028* (2013.01); *A61B 5/6828* (2013.01); *A61B 5/702* (2013.01); *A61B 17/1355* (2013.01)

(58) Field of Classification Search
None
See application file for complete search history.

(56) References Cited

U.S. PATENT DOCUMENTS 6,400,972 B1 * 6/2002 Fine .................... A61B 5/14551
600/310

OTHER PUBLICATIONS

Vontion, et al.,"Physical Fitness and Mitochondrial Respiratory Capacity in Horse Skeletal Muscle", PLOS One, Creative commons Attribution License, Apr. 18, 2012.
Ferrick, et al. "Assay; Measurement of Mitochondrial Function, Extrcellular Flux Assays Quantify Cellular Bioenergetics" Genetic Enineering and Biotechnology News, Nov. 1, 200, vol. 19.
(Continued)

*Primary Examiner* — Eric F Winakur
*Assistant Examiner* — Marjan Fardanesh
(74) *Attorney, Agent, or Firm* — Thomas | Horstemeyer, LLP

(57) ABSTRACT

In one embodiment, measuring mitochondrial capacity includes performing arterial occlusions on a patient, measuring oxygenated hemoglobin/myoglobin and deoxygenated hemoglobin/myoglobin within the patient's body during the occlusions, calculating a blood volume correction factor that accounts for a change in blood volume that occurs during the arterial occlusions, and applying the correction factor to the measured oxygenated hemoglobin/myoglobin and deoxygenated hemoglobin/myoglobin measurements to obtain correct oxygenated hemoglobin/myoglobin and deoxygenated hemoglobin/myoglobin measurements.

12 Claims, 14 Drawing Sheets

(56) References Cited

OTHER PUBLICATIONS

Brand, et al., "Assessing Mitochondrial Dysfuntion in Cells", Biochemical Journal, 435 (Pt 2); 297-312, Mar. 29, 2011.
Lanza, et al., "Mitochondrial Metabolic Function Assessed in Vivo and In Vitro", NIH Public Access, Cur Opin Clin Nutr Metab Care, Sep. 2010, 13 (5): 511-517.
Janssen, Antoon J.M., "Measurment of the Energy-Generating Capacity of Human Muscle Mitochondria: Diagnostic Procedure and Application in Human Pathology", Clinical Chemistry, May 1, 2006.
Conley, et al., "Mitochondrial Function, Fibre Types and Ageing: New Insights from Human Muscle in Vivo", Experimental Physiology, Mar. 1, 2007, 92, 333-339.
Van de Broek, et al., "Increased Mitochondrial Content Rescues in Vivo Muscle Oxidative Capacity in Long-Term High-Fat-Diet-Fed-Rats", Dec. 29, 2009, The FASEB Journal vol. 24, No. 5, 1354-1364.
Kevin R. Short, "Mitochondrial ATP Measurements", Am J Phyiol Regul Integr Comp Physiol 287, 2004. Votion D-M, Gnaiger E, Lemieux H, Mouithys-Mickalad A, Serteyn D (2012) Physical Fitness and Mitochondrial Respiratory Capacity in Horse Skeletal Muscle. PLoS ONE 7(4): e34890. doi:10.1371/journal.pone.
Translational Center for Metabolic Imaging (TCMI); Creating Transformational Tools for Human and Animal in Vivo Studies of Disease.
Brizendine, et al., "Skeletal Muscle Metabolism in Endurance Athletes with Near-Infrared Spectroscopy", American College of Sports Medicine and Exercise; 2013.
Melissa Erickson, et al., "Near-Infrared Assessments of Skeletal Muscle Oxidative Capacity in Persons with Spinal Cord Injury", European Journal of Applied Physiology, Apr. 19, 2013.
Ryan, et al., "Noninvasive Evaluation of Skeletal Muscle Mitochondrial Capacity with Near-Infrared Spectroscopy: correcting for blood volume changes", J. Appl. Physiol 113: 175-183: May 10, 2012.
Ryan, et al. "A Comparison of Exercise Type and Intensity on the Noninvasive Assessment of Skeletal Muscle Mitochondrial Function Using Near-Infrared Spectroscopy", J. Appl. Physiol 114:230-237; Nov. 15, 2012.
Ryan, et al., "Activity-Induced Changes in Skeletal Muscle Metabolism with Optical Spectroscopy", Medicine & Science in Sports & Exercise, Apr. 30, 2013.
Ryan, et al., "Endurance Electrical Stimulation Training Improves Skeletal Muscle Mitochondrial Capacity in Spinal Cord Injury" Elsevier Editorial System(tm) for Archives of Physical Medicine and Rehabilitation Manuscript, Apr. 29, 2013.
McCully, et al., "Relationships between in Vivo and in Vitro Measurements of the Metabolism in Young and Old Human Calf Muscles", J. Appl Physiol 75: 813-819, 1993.
Nagasawa, et al., "A Practical Indicator of Muscle Oxidative Capacity Determined by Recovery of Muscle $O_2$ Consumption Using NIR Spectroscopy", European Journal of Sport Science, Aug. 25, 2011.
McCully, et al., "Near-Infrared Spectroscopy: What Can it Tell Us About Oxygen Saturation in Skeletal Muscle?" Exercise and Sport Sciences Reviews, Mar. 28, 2000.
Dranka, et al., "Mitochondria! Reserve Capacity in Endothelial Cells: the Impace of Nitric Oxide and Reactive Oxygen Species", Department of Pathology and Center for Free Radical Biology, University of Alabama, (2010), 905-914.

\* cited by examiner

SYSTEMS AND METHODS FOR MEASURING MITOCHONDRIAL CAPACITY

CROSS-REFERENCE TO RELATED APPLICATION(S)

This application is a divisional application of co-pending U.S. Non-Provisional application entitled, "Systems And Methods For Measuring Mitochondrial Capacity," having Ser. No. 13/793,558 and filed Mar. 11, 2013, and claims priority to U.S. Provisional Application Ser. No. 61/609,025, filed Mar. 9, 2012, both of which are hereby incorporated by reference herein in their entireties.

NOTICE OF GOVERNMENT-SPONSORED RESEARCH

This invention was made with Government support under grant number 2R01HD039676-09A2, awarded by the National Institutes of Health. The Government has certain rights in the invention.

BACKGROUND

Measuring skeletal muscle oxidative metabolism has been important in understanding muscle function in health and disease. For example, it is important to be able to measure muscle oxidative metabolism in spinal cord accident victims both before and after therapy, which may include the administration of one or more drugs that are under evaluation.

Noninvasive methodologies have enhanced the study of mitochondrial function, particularly in human participants. The primary noninvasive method of measuring mitochondrial function has been magnetic resonance spectroscopy (MRS) and more particularly the use of the kinetics of phosphocreatine (PCr) resynthesis after exercise as a direct assessment of mitochondrial capacity. Although MRS can provide an accurate indication of mitochondrial capacity, MRS is a costly technique that requires large, expensive equipment and a high level of technical expertise.

Near-infrared spectroscopy (NIRS) also provides a noninvasive measure of muscle oxygenation. Commercially available NIRS devices typically provide information about the relative changes in oxygenated hemoglobin/myoglobin ($O_2Hb$), deoxygenated hemoglobin/myoglobin (HHb), and total hemoglobin or blood volume (tHb). In comparison to MRS equipment, NIRS devices are much smaller, less expensive, portable, and easier to use, making them more practically useful for a clinical setting.

NIRS measurement of skeletal muscle oxygen consumption has been conducted using both venous and arterial occlusions. In the typical procedure, blood flow through the veins and arteries is halted by the application of a cuff, and measurements are then taken with the NIRS device to quantify the oxygen that is being consumed by the muscle. Although it is typically assumed that the cuff stops all blood flow, in reality blood still flows into the smaller blood vessels, such as the capillaries, due to the pressure differential between the blood within the arteries and the smaller vessels. Such blood flow is associated with a change in blood volume that can skew the other measurements taken by the NIRS device. In order for the arterial occlusion method of measuring skeletal muscle oxygen consumption to be accurate, there should be little or no change in blood volume, tHb.

From the above discussion, it can be appreciated that it would be desirable to have a system and method for measuring skeletal muscle oxygen consumption using NIRS that compensates for changes in blood volume and, therefore, provides more accurate measurements.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
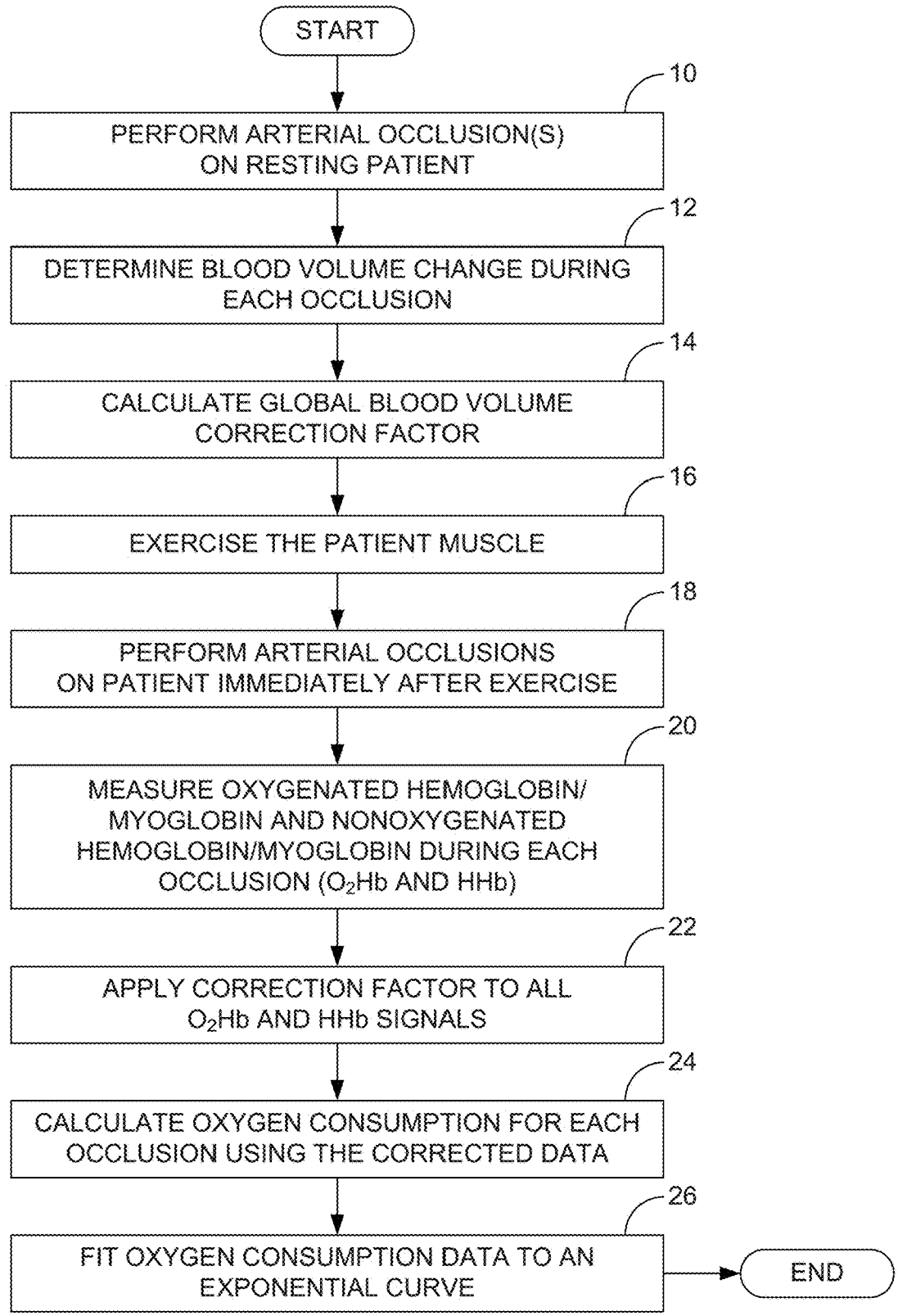
FIG. 1 is a flow diagram of a first embodiment of a method for measuring mitochondrial capacity.

As described above, it would be desirable to have a system and method for measuring skeletal muscle oxygen consumption using near-infrared spectroscopy (NIRS) that compensates for changes in blood volume. Disclosed herein are NIRS systems and methods that take such blood volume changes into account. More particularly, the volume change can be taken into account by adjusting the measured data so that the decrease in the oxygenated hemoglobin/myoglobin signal is equivalent to the increase in the deoxygenated hemoglobin/myoglobin signal to reflect the symmetry of the mitochondrial oxygen consumption that actually occurs within the body. In a first embodiment, an average correction factor is calculated from a series of resting arterial occlusions. In a second embodiment, individualized correction factors are calculated for each individual arterial occlusion after exercise. In a third embodiment, an iterative routine is used to calculate the correction factor.

In the following disclosure, various specific embodiments are described. It is to be understood that those embodiments are example implementations of the disclosed inventions and that alternative embodiments are possible. All such embodiments are intended to fall within the scope of this disclosure.

Introduction

NIRS provides signals that represent the two oxygenation states of hemoglobin: oxygenated and deoxygenated. The NIRS signals come from small vessels, such as terminal arterioles, capillaries, and collecting venules. For venous and arterial occlusions to accurately measure oxygen consumption (either as the disappearance of the oxygenated NIRS signal or the appearance of the deoxygenated NIRS signal), the metabolic use of oxygen at a cellular level (i.e., within the mitochondria) should result in a symmetrical change in the oxygenated and deoxygenated NIRS signals. However, the continuous supply of hemoglobin from high-pressure larger arteries to the small vessels results in the invalid measurement of oxygen consumption due to the resulting blood volume changes (i.e., increases).

Described herein are systems and methods that can be used to correct for such volume changes. In the systems and methods, a blood volume correction factor ($\beta$) is calculated based on the assumption that, during an arterial occlusion, changes in the collected data for oxygenated hemoglobin/myoglobin ($O_2Hb$) and deoxygenated hemoglobin/myoglobin ($HHb$) occur with a 1:1 ratio that represents mitochondrial oxygen consumption only (i.e., no arterial oxygen delivery or venous return of deoxygenated blood). The arterial occlusions can be achieved through the application of a blood pressure cuff. It is assumed that inflation of the cuff completely blocks the arterial delivery and venous return of blood. The equation below describes the calculation for the correction factor:

$$\beta_i = \frac{|O_2Hb_i|}{(|O_2Hb_i| + |HHb_i|)} \quad \text{[Equation 1]}$$

In Equation 1, $\beta$ is the blood volume correction factor, i represents the arterial occlusion of interest, $O_2Hb$ is the oxygenated hemoglobin/myoglobin signal, and $HHb$ is the deoxygenated hemoglobin/myoglobin signal.

The correction factor can be determined using various approaches. Once has been defined, it can be applied to the data using the following equations:

$$O_2Hb_c = O_2Hb - [tHb*(1-\beta)] \quad \text{[Equation 2]}$$

$$HHb_c = HHb - (tHb*\beta) \quad \text{[Equation 3]}$$

where $O_2Hb_c$ and $HHb_c$ are the corrected oxygenated and deoxygenated hemoglobin/myoglobin signals respectively, tHb is the arithmetic sum of the uncorrected $O_2Hb$ and $HHb$, and $\beta$ is the blood volume correction factor.

Example Methods for Blood Volume Correction

Three methods have been developed to correct for the blood volume change. The underlying theme behind each method is the direct exchange between the oxygenated and deoxygenated NIRS signals.

In a first method, one or more resting occlusions are performed and the proportion of blood volume signal attributed to the oxygenated and deoxygenated NIRS signals is calculated using a resting arterial cuff (or multiple cuffs to reduce variance) for which the correction factors are calculated. The correction factors are then applied to the NIRS signals (oxygenated and deoxygenated) before calculating the rate of oxygen consumption. The slope of change in the corrected oxygenated and deoxygenated signals will then be equal and will only represent oxygen consumption by the mitochondria. After calculating the rate of oxygen consumption for a series of post-exercise cuffs, an exponential curve fitting routine is applied to the measured data to produce the measurement of mitochondrial capacity.

Figure 5:
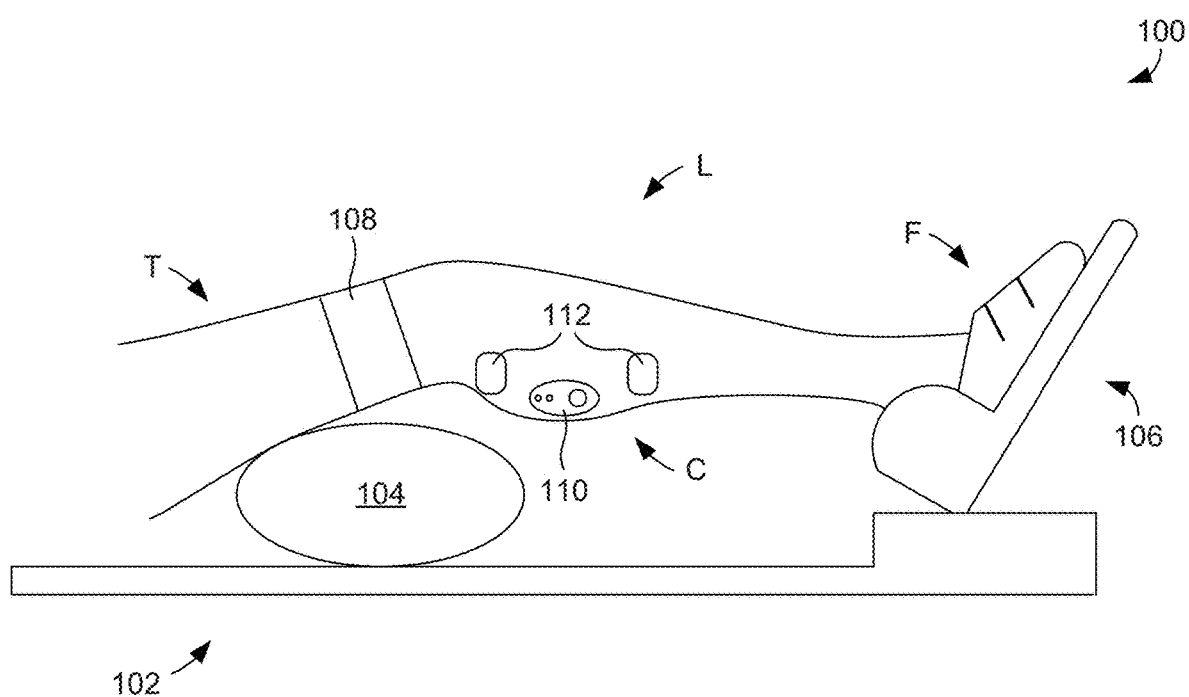
FIG. 5 is a schematic drawing of an embodiment of apparatus for taking measurements on the gastrocnemius muscle.

FIG. 1 describes an example of such a method. Beginning with block 10, one or more arterial occlusions are performed on a resting patient. In some embodiments, the occlusions can be achieved using a blood pressure cuff, as shown in FIG. 5. In FIG. 5, apparatus 100 includes a platform 102 on which a patient is supported. The patient's leg L rests on a support 104, such as a pillow, and the patient's foot F is secured with a foot brace 106. A blood pressure cuff 108 is applied to the thigh T to occlude arterial blood flow. An NIRS device, in the form of a sensor 110, is applied to the calf C as are electrodes 112. By way of example, approximately 1 to 5 occlusions each having a duration of approximately 5 to 60 seconds can be performed. Because the patient is at rest and has not performed any exercise immediately prior to the occlusions, the occlusions may be referred to as "resting cuffs." Referring to block 12, the blood volume change that occurs during each occlusion is determined. The volume change can be measured using the NIRS device. Specifically, the tHb signal is the oxygenated hemoglobin/myoglobin signal and the hemoglobin/myoglobin deoxygenated signal combined (i.e., the arithmetic sum), which provides an indication of the total blood volume in the area. The signal will increase during the occlusion as the blood volume in the area increases and therefore provides an indication of the blood volume change.

Referring next to block 14, a global blood volume correction factor $\beta$ is calculated. The correction factor is calculated as the proportion of the blood volume change attributed to both the oxygenated ($\beta$) and deoxygenated ($1-\beta$) during the resting arterial occlusions. In some embodiments, $\beta$ is calculated using Equation 1 described above. That correction factor will be used on all oxygenated and deoxygenated signals that will be subsequently captured.

With reference to block 16, the patient muscle is exercised. The exercise need not be maximal exercise to exhaustion. Instead, a moderate amount of exercise that is sufficient to raise the muscle's metabolic rate is sufficient. In some embodiments, the patient can manually exercise (i.e., flex) the muscle. In other embodiments, the muscle can be exercised through the application of external electrical stimulation.

Immediately following the exercise, multiple arterial occlusions are performed on the patient, as indicated in block 18. Again, the occlusions can be achieved using a cuff, such as that shown in FIG. 5. By way of example, approximately 8 to 25 occlusions each having a duration of approximately 5 to 10 seconds can be performed depending on how rapidly the muscle recovers after exercise (slower recovery may require more occlusions). As each cuff is performed, the oxygenated hemoglobin/myoglobin and the deoxygenated hemoglobin/myoglobin are measured, as indicated in block 20. In some embodiments, both can be measured using an NIRS device, such as the sensor 110 shown in FIG. 5, in which case the signals $O_2Hb$ and $HHb$ are obtained. By way of example, these signals can be obtained during the cuffs at a frequency of approximately 1 to 250 Hz.

After all of the oxygenated and deoxygenated signals have been collected, the blood correction factor is applied to each of the signals, as indicated in block 22. In some embodiments, the correction factor is applied using Equations 2 and 3 described above.

With reference next to block 24, the oxygen consumption for each occlusion can be calculated using the corrected oxygenated and deoxygenated signals. In some embodiments, the oxygen consumption is calculated using $$\frac{\Delta O_2 Hb}{\Delta \text{time}} \text{ and } \frac{\Delta HHb}{\Delta \text{time}}.$$

Finally, with reference to block 26, the oxygen consumption data is fit to an exponential curve to obtain a representation of mitochondrial function.

In a second method, a process similar to that performed in the first method is performed. However, in the second method, individualized correction factors β (instead of a global correction factor) are calculated for every occlusion measurement of oxygen consumption. These correction factors are simply the proportion of blood volume signal attributed to the oxygenated and deoxygenated NIRS signals for each cuff. This means that each individual data point has its own correction factor. After each measurement of oxygen consumption is corrected for blood volume, the measurements can be run through the exponential curve fitting routine to generate the mitochondrial capacity measurement.

Figure 2:
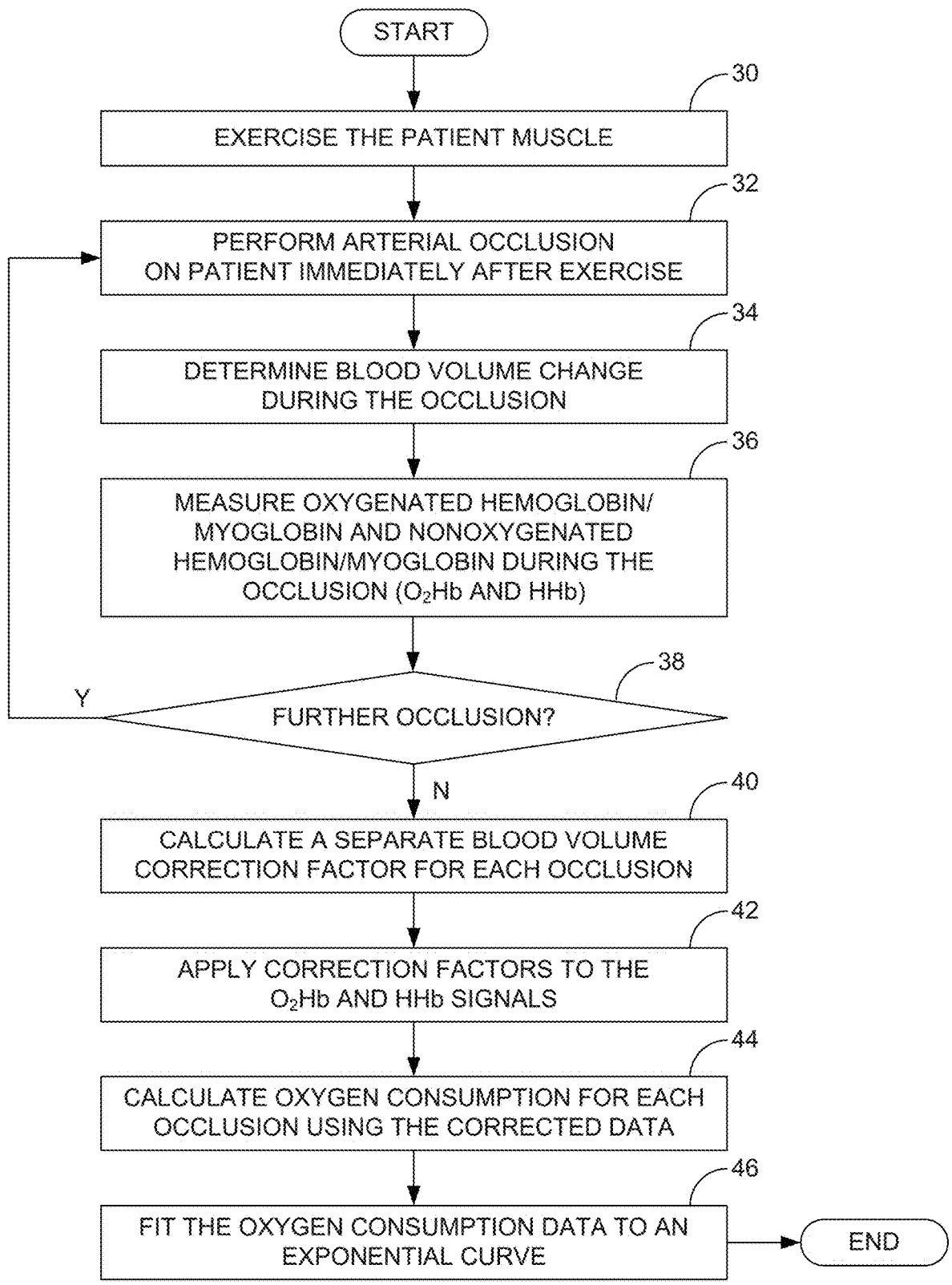
FIG. 2 is a flow diagram of a second embodiment of a method for measuring mitochondrial capacity.

FIG. 2 describes an example of such a method. Beginning with block 30, the patient muscle is exercised. As before, a moderate amount of exercise that raises the muscle's metabolic rate is sufficient. Immediately following the exercise, an arterial occlusion is performed on the patient, as indicated in block 32. For each occlusion, the blood volume change is determined, as indicated in block 34. As before, the volume change can be measured using the NIRS device by obtaining the tHb signal, which increases during the occlusions as the blood volume increases. Simultaneous to measuring the blood volume change during each occlusion, the oxygenated hemoglobin/myoglobin and the deoxygenated hemoglobin/myoglobin signals are measured, as indicated in block 36. As before, both can be measured using an NIRS device, in which case the signals $O_2Hb$ and $HHb$ are obtained.

As indicated in block 38, the process of blocks 32-36 is repeated for each occlusion. By way of example, approximately 8 to 25 occlusions each having a duration of approximately 5 to 10 seconds can be performed depending on how rapidly the muscle recovers after exercise (slower recovery may require more occlusions). Once each desired occlusion has been performed, flow continues to block 40 at which a separate blood volume correction factor β is calculated for each occlusion using the measured blood volume change so that each individual data point from the NIRS device (both $O_2Hb$ and $HHb$) receives an individualized correction based on the blood volume (tHB) corresponding with the data point. As before, the correction factor can be calculated using Equation 1 described above. Once the various correction factors have been calculated, they can be applied individually to the oxygenated and deoxygenated signals, as indicated in block 42. As before, the correction factor is applied to individual data points ($O_2Hb$ and $HHb$) using Equations 2 and 3 described above.

At this point, the oxygen consumption for each occlusion can be calculated using the corrected oxygenated and deoxygenated signals (block 44), and the oxygen consumption data is fit to an exponential curve that represents mitochondrial function (block 46).

In a third method, post-processing is performed on the recovery curves that are generated. In particular, the method involves the calculation of oxygen consumption (slopes of oxygenated and deoxygenated signals) from raw NIRS data. The raw (uncorrected) measurements of oxygen consumption are fit to an exponential curve using the curve fitting routine. A Nelder-Mead algorithm is then used to iteratively search for the blood volume correction factor that results in the smallest error (e.g., least squares error) for the difference between the oxygenated and deoxygenated recovery curves. This method differs from the previous two methods because, since it enables post-processing correction for blood volume in recovery data, the raw infrared data are not required.

Figure 3:
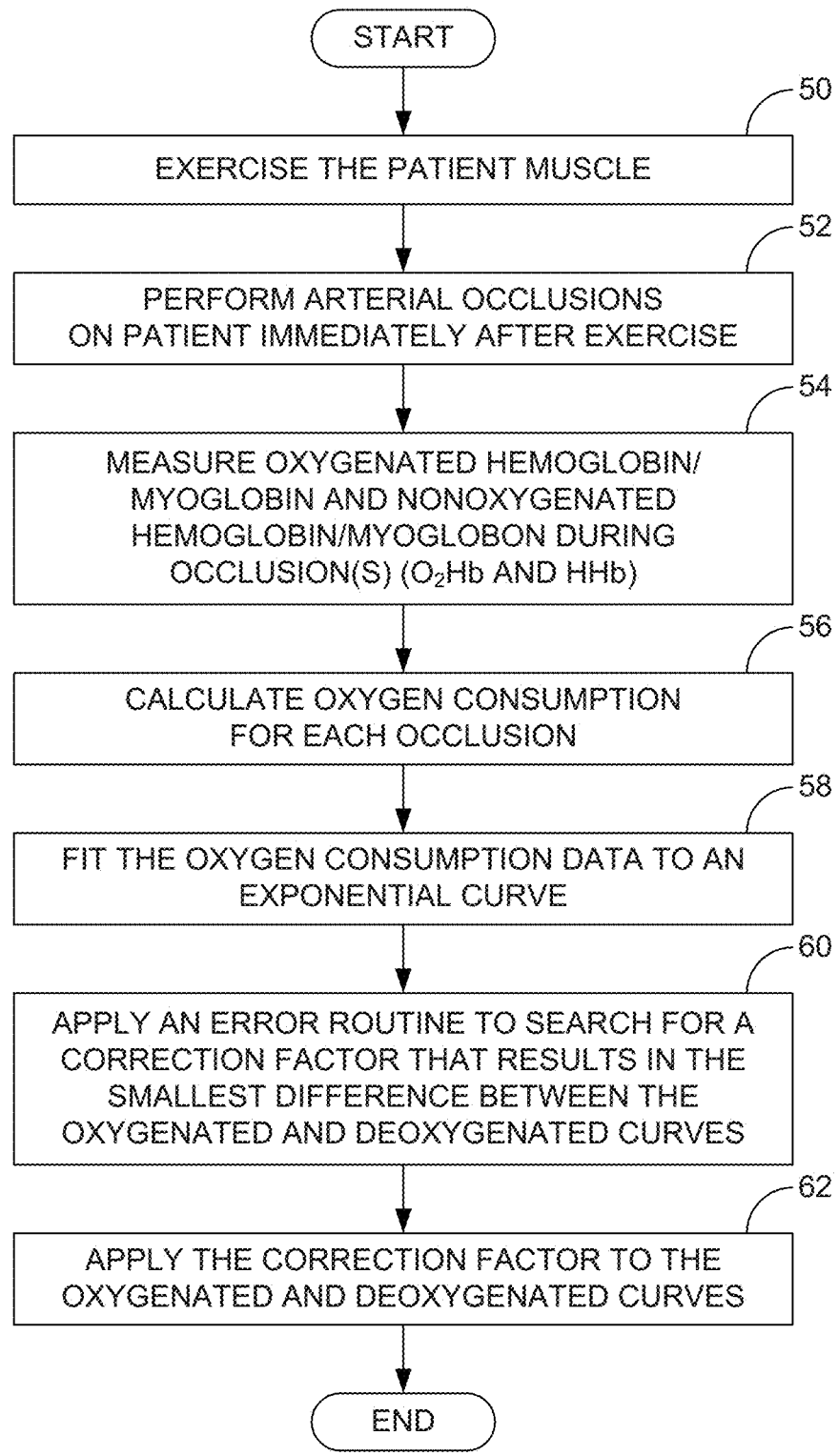
FIG. 3 is a flow diagram of a third method of an embodiment for measuring mitochondrial capacity.

FIG. 3 describes an example of such a method. As in the other methods, the patient muscle is exercised (block 50), one or more arterial occlusions are performed (block 52), and the oxygenated hemoglobin/myoglobin and the deoxygenated hemoglobin/myoglobin signals are measured (block 54). Next, the oxygen consumption for each occlusion is calculated (block 56) and the oxygen consumption data is fit to an exponential curve that represents mitochondrial function (block 58).

In the third embodiment, however, an error routine is then applied to the oxygenated and deoxygenated data to search for a blood volume correction factor β that results in the smallest difference between the oxygenated and deoxygenated recovery curves, as indicated in block 60. In some embodiments, a Nelder-Mead algorithm is used to iteratively search for the blood volume correction factor that results in the smallest least squares for the difference between the oxygenated and deoxygenated curves. Once that correction factor has been determined, it is applied to the oxygenated and deoxygenated curves, as indicated in block 62.

Figure 4:
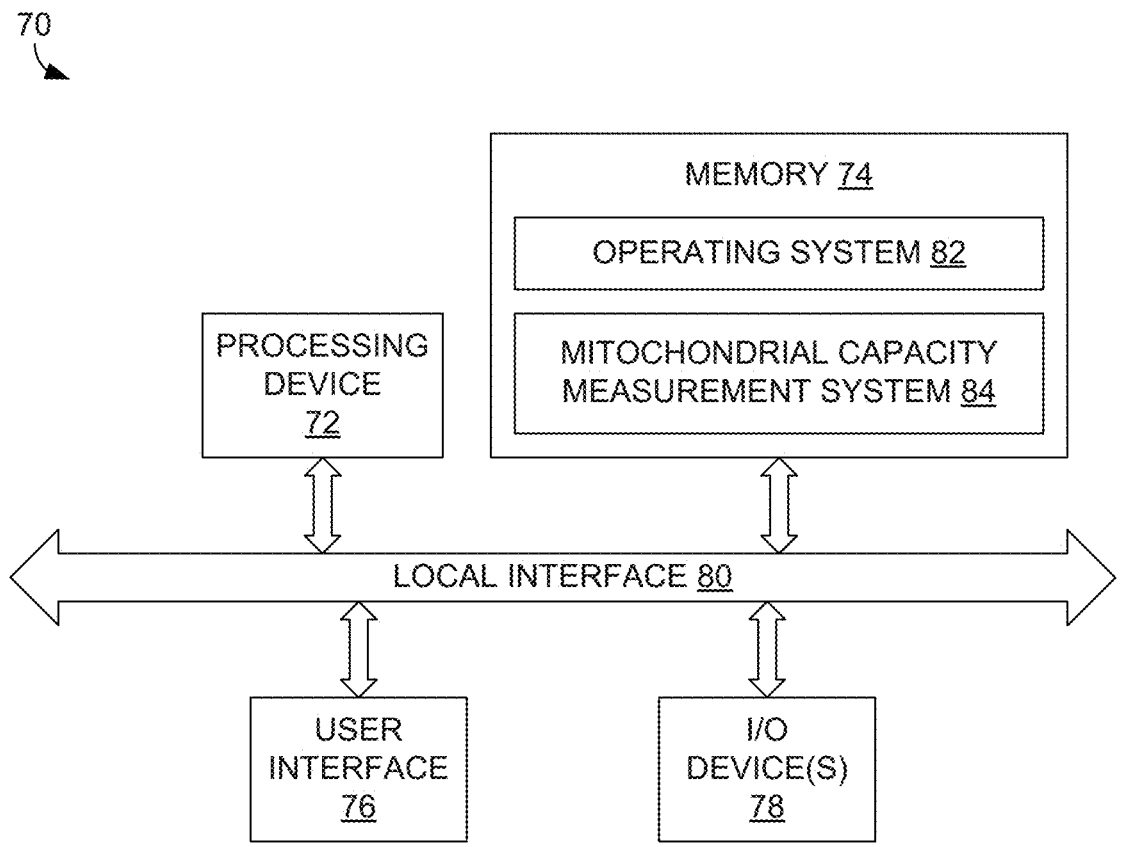
FIG. 4 is a block diagram of a computing device that can be used to perform at least some of the method steps described in relation to FIGS. 1-3.

FIG. 4 illustrates an example configuration for a computing device 70 that can be used to perform at least some of the method steps described above in relation to FIGS. 1-3. As is shown in FIG. 4, the computing device 70 comprises a processing device 72, memory 74, a user interface 76, and at least one I/O device 78, each of which is connected to a local interface 80.

The processing device 72 can include a central processing unit (CPU) or a semiconductor based microprocessor (in the form of a microchip). The memory 74 includes any one of or a combination of volatile memory elements (e.g., RAM) and nonvolatile memory elements (e.g., hard disk, ROM, tape, etc.). The user interface 76 comprises the components with which a user interacts with the computing device 70, and the I/O devices 78 are adapted to facilitate communication with other devices.

The memory 74 comprises programs (i.e., logic) including an operating system 82 and one or more blood volume correction algorithms 84. The algorithms 84 are configured to receive the data collected by the NIRS device and analyze the data to generate and apply one or more correction factors β that are used to output more accurate indications of mitochondrial activity.

Testing

The blood volume correction described above was applied to data from a variety of subjects including healthy college-aged participants (both recreationally active and sedentary) and clinical populations, such as spinal cord injury patients. The reliability and test-retest reproducibility of the measurements in young, healthy individuals was also evaluated. The testing and results are described below.

Twenty-four subjects (14 male, 10 female) were tested in the study. Subjects were chosen to represent a wide variety of muscle oxidative capacity and included college-aged endurance trained and sedentary subjects, as well as four individuals with chronic spinal cord injury (SCI). Ten healthy, young subjects (6 male, 4 female) were tested on two separate days over a period of one week to assess the reliability and reproducibility of the measurements.

Each subject was placed on a padded table, supine, with both legs extended (0° of flexion). The right foot was placed into a custom-built isometric exercise device to limit motion artifact in the NIRS signal (see FIG. 5). The foot was strapped firmly to the exercise device using non-elastic hook-and-loop straps proximal to the base of the fifth digit, and the knee was supported. An NIRS optode (probe) was placed at the level of the largest circumference of the muscle of interest (medial gastrocnemius or vastus lateralis) and secured with hook-and-loop straps and adhesive tape. Four aluminum foil electrodes connected to a Theratouch 4.7 stimulator (Rich-mar, Inola, Okla.) were placed on the skin, two proximal and two distal to the NIRS optode. A blood pressure cuff (Hokanson E20 cuff inflator; Bellevue, Wash.) was placed proximal to the NIRS optode.

Testing was performed on one visit to the laboratory. Subjects who participated in the reproducibility study were tested on a second occasion 3-7 days after the first session. Adipose tissue thickness (ATT) was measured at the site of the NIRS optode using B-mode ultrasound (LOGIQ e; GE HealthCare, USA). Subjects were instructed not to consume caffeine or tobacco on the day of the test or to use alcohol or perform moderate or heavy physical activity for at least 24 hours before the test.

The test protocol included a baseline measurement of muscle oxygenation, followed by inflation of a blood pressure cuff (250-300 mmHg) for the measurement of resting muscle oxygen consumption. To increase $mVO_2$, 15 seconds of continuous electrical stimulation at 4 Hz was applied to the muscle. The current intensity was adjusted for each individual to produce twitch contractions at the maximal tolerable level. Pilot experiments suggested that small differences in stimulation level did not influence measurements of metabolic rate. Immediately following the electrical stimulation, a series of 10-18 brief (5-10 seconds) arterial occlusions were applied to measure the rate of recovery of $mVO_2$ back to resting levels. Finally, to normalize the NIRS signal, a 3-5 minute arterial occlusion was applied to completely deoxygenate the tissue under the optode (i.e., 0% oxygenation) and the peak hyperemic response upon release of the cuff was used to indicate 100% oxygenation (see FIG. 6). A five-second electrical stimulation period was performed prior to this 3-5 minute arterial occlusion to increase metabolic rate, thereby minimizing the duration of the arterial occlusion and the discomfort imposed on the participants.

NIRS signals were obtained using a continuous wave NIRS device (Oxymon MK III, Artinis Medical Systems, The Netherlands) having two channels (two equivalent pulsed light sources, two avalanche photodiode detectors, shielded from ambient light), using an intensity-modulated light at a frequency of 1 MHz and laser diodes at 3 wavelengths (905, 850, and 770 nm) corresponding to the absorption wavelengths of oxyhemoglobin ($O_2Hb$) and deoxyhemoglobin (HHb), with an autosensing power supply (approximately 40 W at 110-240 V). The probe was set for two source-detector separation distances after measurement of adipose tissue thickness. The NIRS data was collected at 10 Hz.

$mVO_2$ was calculated as the slope of change in $O_2Hb$ and HHb during the arterial occlusion using simple linear regression. $mVO_2$ was calculated in absolute units using a differential pathlength factor (DPF) of 4, as suggested by the manufacturer. $mVO_2$ was also expressed as a percentage of the ischemic calibration per unit time. This measurement was made at rest and repeated a number of times after exercise. The post-exercise repeated measurements of $mVO_2$ were fit to a mono-exponential curve according to the formula below:

$$y = \text{End} - \text{Delta} * e^{-1/Tc} \quad \text{[Equation 4]}$$

In Equation 4, y represents relative $mVO_2$ during the arterial occlusion, End is the $mVO_2$ immediately after the cessation of exercise, Delta is the change in $mVO_2$ from rest to end exercise, and Tc is the fitting time constant.

All subjects were able to complete testing with no adverse events. The physical characteristics of participants are shown in Table 1.

TABLE 1

| Muscle Tested | Height (cm) | Weight (kg) | Age (yr) | Gender (M/F) | ATT (mm) |
| --- | --- | --- | --- | --- | --- |
| Medial Gastrocnemius (n = 10) | 172.8 ± 6.9 | 67.5 ± 7.7 | 23.3 ± 3.0 | 6 M /4 F | 6.0 ± 1.6 |
| Vastus Lateralis (n = 14) | 175.2 ± 12.8 | 71.2 ± 16.0 | 35.5 ± 15.4 | 8 M/6 F | 8.0 ± 2.8 |

Figure 6:
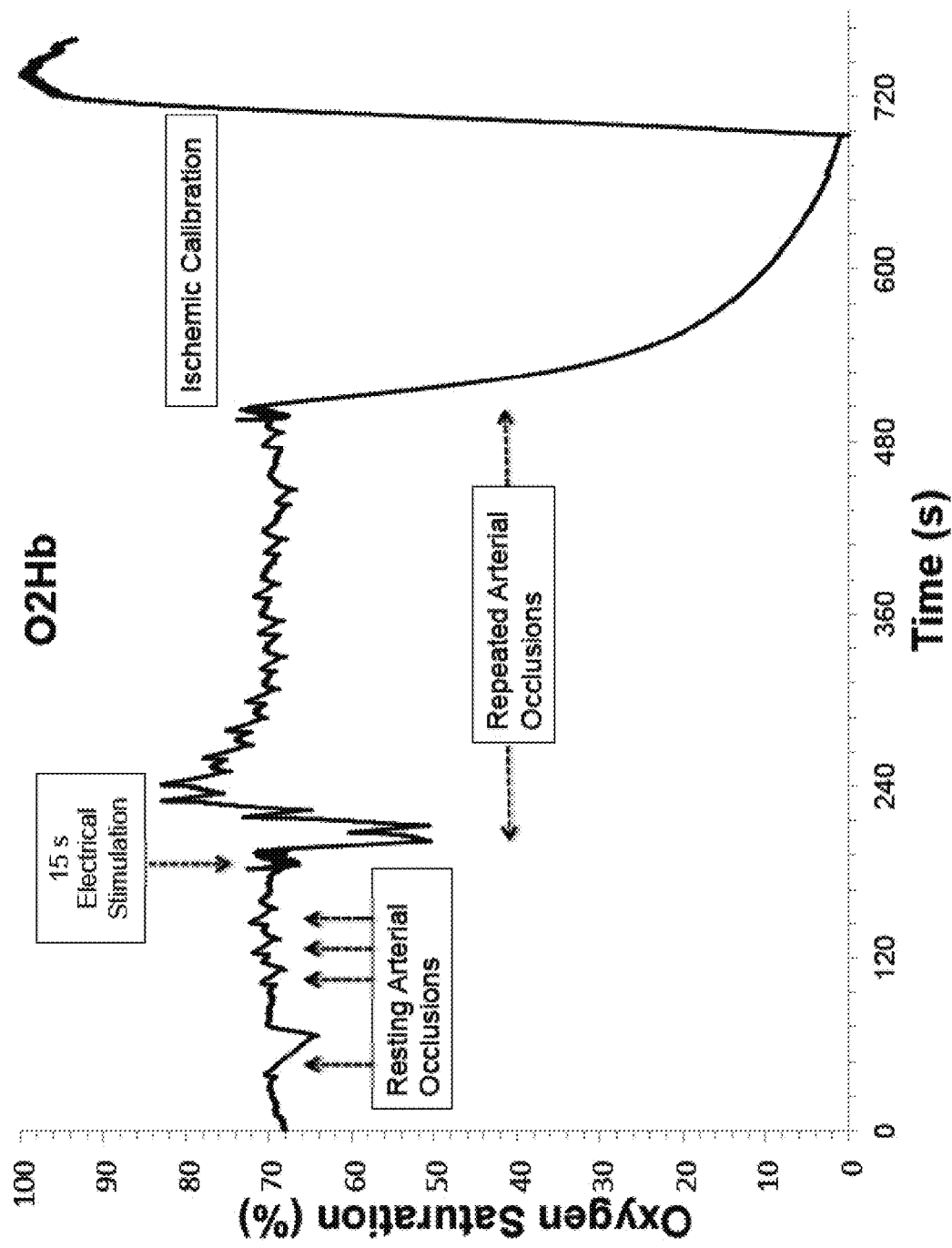
FIG. 6 is a graph that plots muscle oxygenated hemoglobin/myoglobin during rest, resting arterial occlusions, and a 15-second electrical stimulation exercise followed by a series of transient arterial occlusions after exercise.
Figure 7A:
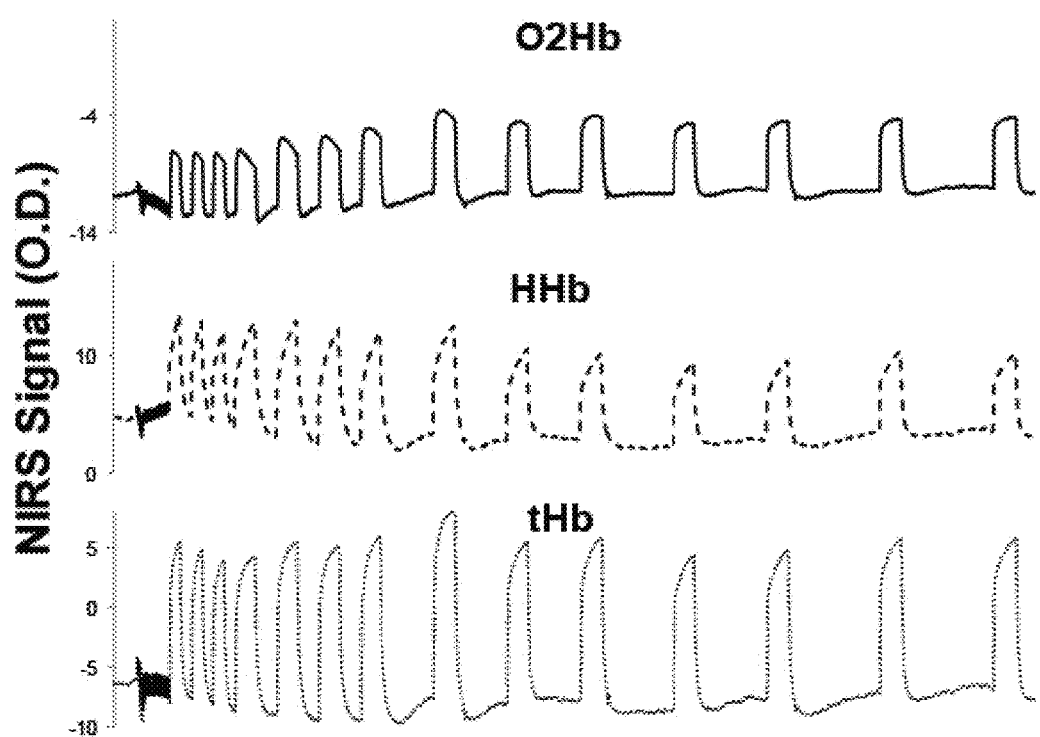
FIGS. 7A-7F comprises graphs that plot post-exercise arterial occlusion data for the oxygenated hemoglobin/myoglobin ($O_2Hb$), deoxygenated hemoglobin/myoglobin (HHb), and the blood volume (tHb) signals for an individual uncorrected (A) and with a blood volume correction (B). Magnification of the final two cuffs for uncorrected (C) and corrected (D) signals are also shown. Mono-exponential recovery curves are also shown for uncorrected (E) and corrected (F) data.
Figure 7B:
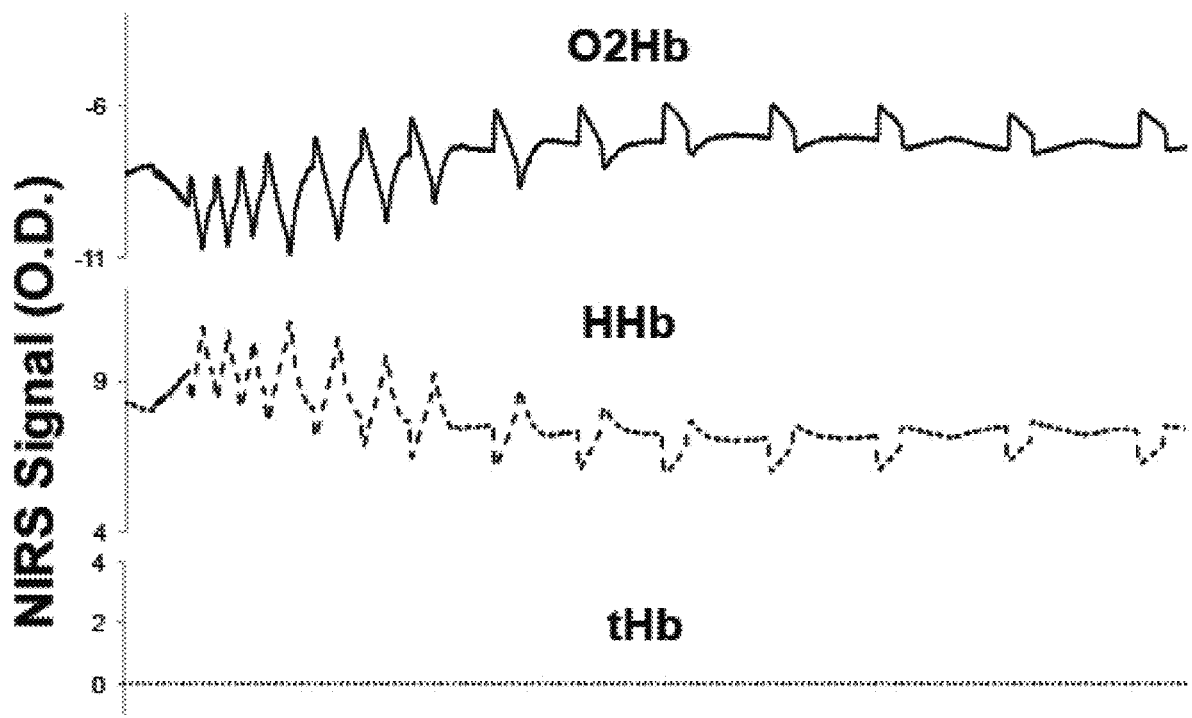
Figure 7C:
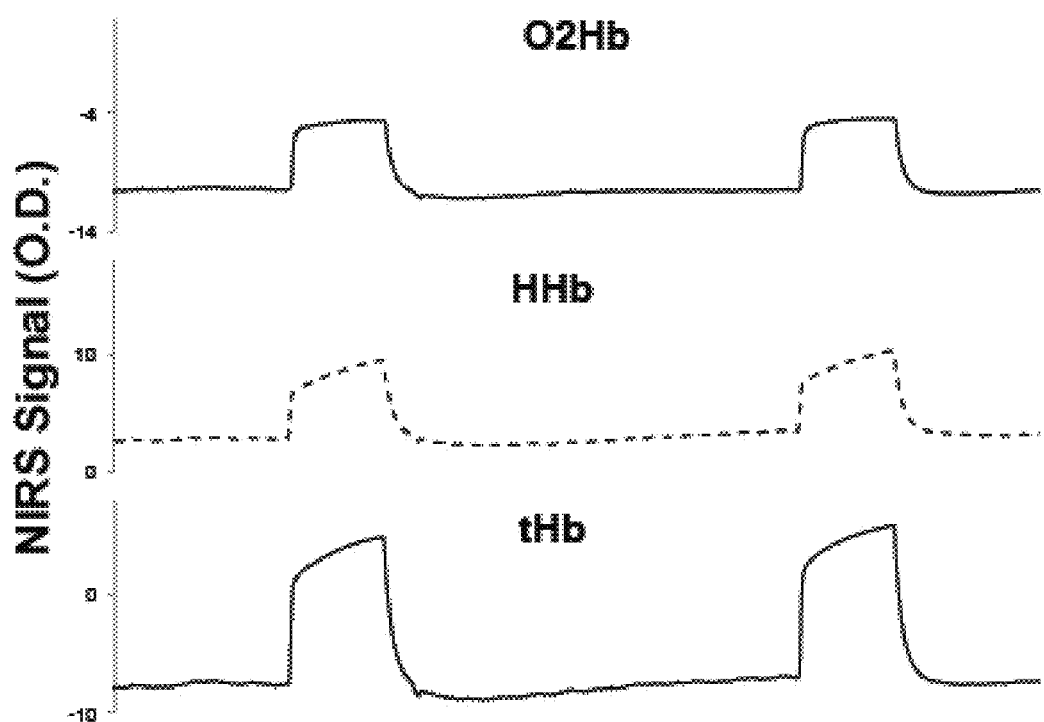
Figure 7D:
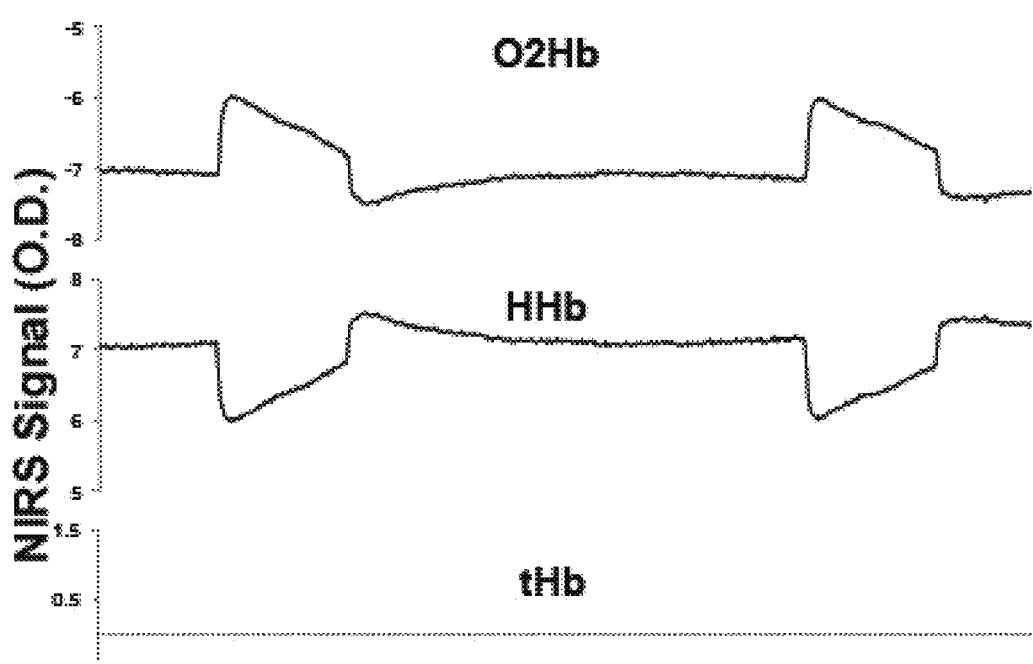
Figure 7E:
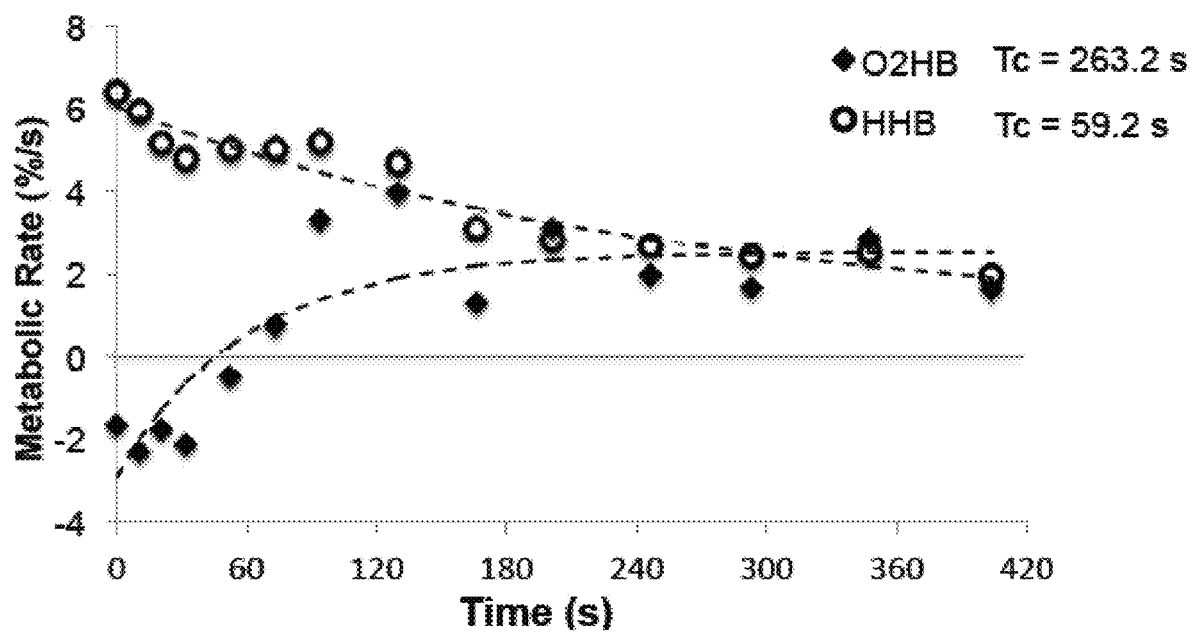
Figure 7F:
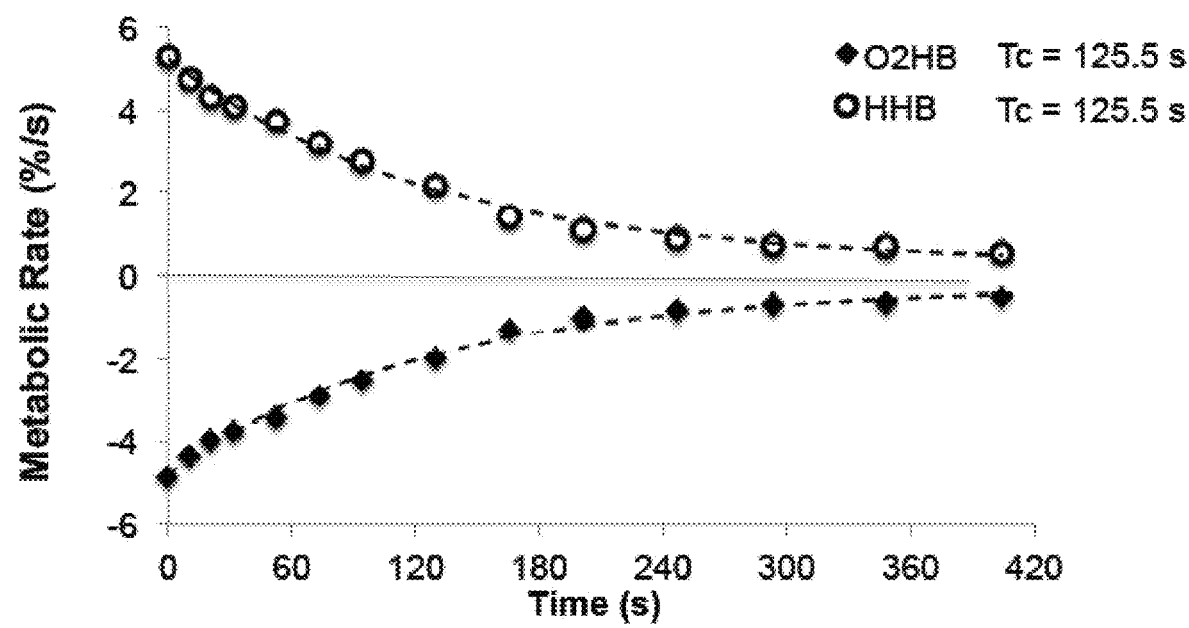

All patient data were analyzed using the three approaches described above for correction of the blood volume influence on the NIRS signal. There were no differences in resting, post-exercise $mVO_2$, or the recovery time constant using the three methods (p=0.39). Therefore, the remainder of the results was presented using the second approach (i.e., individualized β's for each arterial occlusion; FIG. 6). The application of the blood volume correction can be seen in FIG. 7.

Figure 8A:
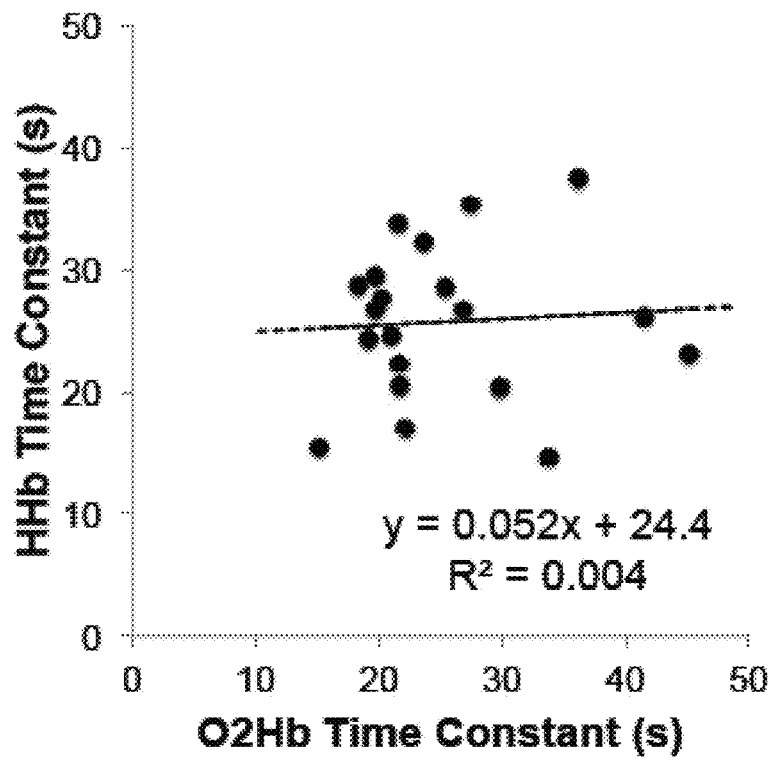
FIGS. 8A and 8B comprises graphs that show comparisons between the recovery time constants for the oxygenated hemoglobin/myoglobin ($O_2Hb$) and deoxygenated hemoglobin/myoglobin (HHb) signals without (A) and with (B) blood volume correction.
Figure 8B:
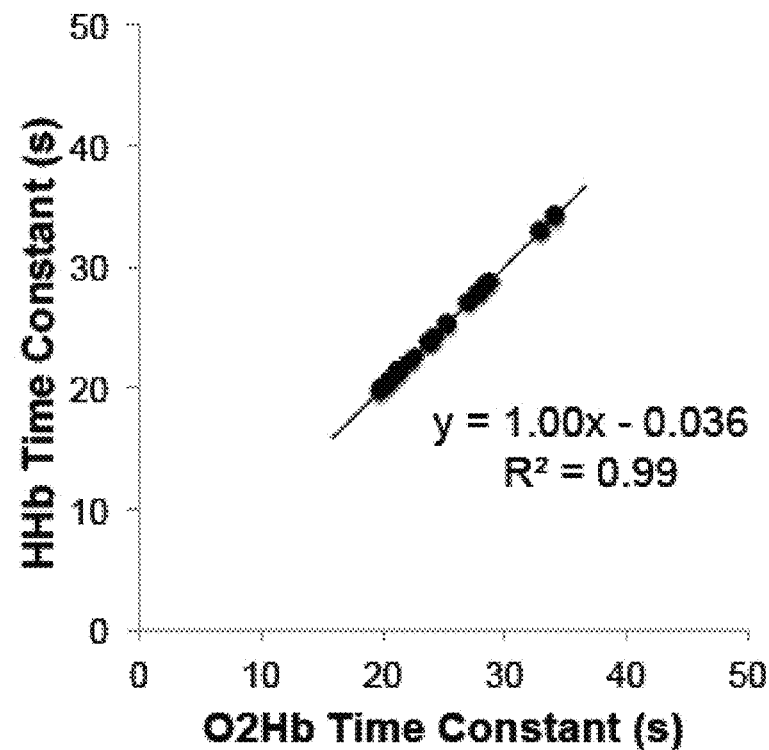

Without correcting for blood volume, there was an unequal change in the $O_2Hb$ and HHb signals during arterial occlusions in nearly all of the tests. No relationship between the recovery time constants for the $O_2Hb$ and HHb signals (p=0.78) were found without the blood volume correction (FIG. 8A). When correcting for blood volume, there is a strong relationship between the $O_2Hb$ and HHb (p<0.001), as shown in FIG. 8B. It was determined, however, that the O₂Hb signal is more susceptible to blood volume changes than the HHb signal in most cases. Because the raw data, uncorrected for blood volume, were deemed unreliable, they were excluded from the remainder of the analysis. The average β for all subjects and all test days was 0.52±0.21 (mean±SD) with a range from 0.07 to 0.92.

The reproducibility of the NIRS measurements for resting mVO₂ and the end-exercise recovery of mVO₂ was investigated by testing 10 individuals on two separate occasions. All values for resting mVO₂ and the recovery of mVO₂, as well as the coefficient of variation and intraclass correlation coefficient, are shown in Table 2.

TABLE 2

|  | Test 1 | Test 2 | Mean CV (%) | ICC (95% CI) |
|---|---|---|---|---|
| Resting mVO₂ (% s⁻¹) O2HB |  |  |  |  |
| Uncorrected | 0.25 ± .11 | 0.24 ± .17 | 31.4 | −0.44 |
| Corrected | 0.28 ± .08 | 0.28 ± .11 | 2.4 | 0.19 |
| HHB |  |  |  |  |
| Uncorrected | 0.32 ± .11 | 0.33 ± .12 | 10.7 | 0.08 |
| Corrected | 0.28 ± 0.8 | 0.28 ± .11 | 2.4 | 0.19 |
| End-exercise Recovery O2HB Tc (s) |  |  |  |  |
| Uncorrected | 24.3 ± 8.2 | 23.7 ± 6.1 | 21.0 | 0.14 |
| Corrected | 24.5 ± 4.0 | 22.1 ± 2.1 | 10.6 | 0.68 |
| HHB Tc (s) |  |  |  |  |
| Uncorrected | 28.3 ± 7.6 | 23.3 ± 7.6 | 20.63 | 0.57 |
| Corrected | 24.5 ± 4.0 | 22.1 ± 2.1 | 10.6 | 0.67 |

Figure 9A:
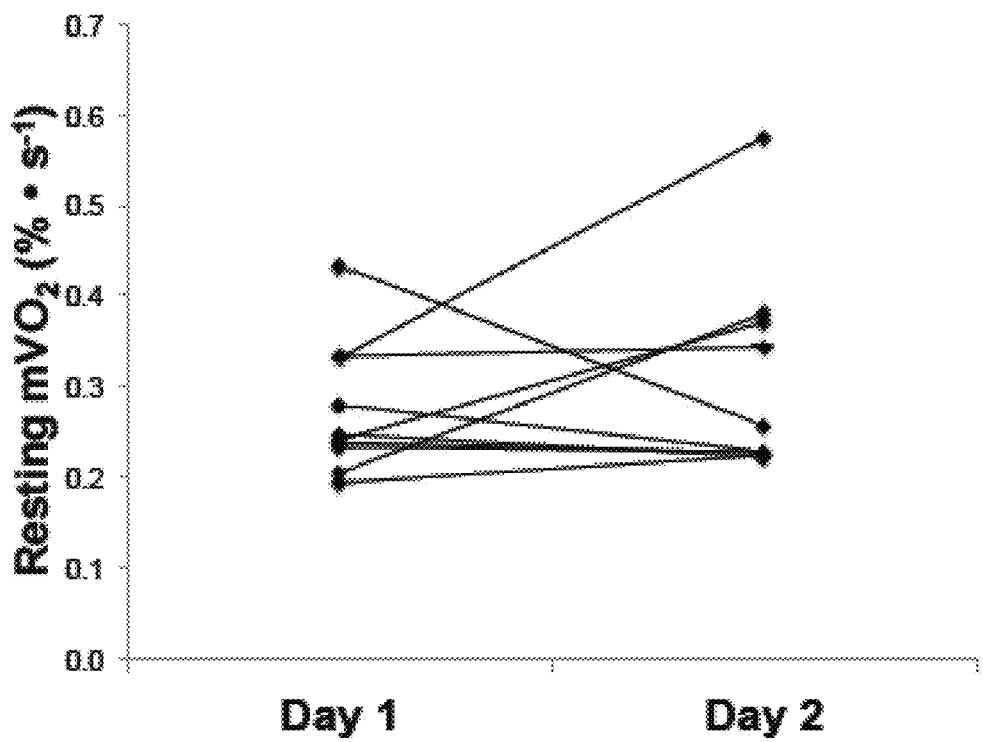
FIGS. 9A and 9B comprises graphs that illustrate (A) reproducibility results for resting muscle oxygen consumption and (B) the post-exercise recovery time constant of muscle oxygen consumption for two different days (i.e., Day 1 and Day 2).

Resting oxygen consumption was measured by NIRS during an arterial occlusion (~270 mmHg). Resting mVO₂ of all participants from Day 1 and Day 2 is shown in FIG. 9A. The mean within-subject CV for comparison between days was 2.4% (range 1-32%). There was no difference in resting oxygen consumption between the vastus medialis and gastrocnemius muscles. The reliability and reproducibility of resting mVO₂ from a single arterial occlusion (~30 seconds) with the average of three 10-second arterial occlusions were compared (see FIG. 6). Averaging the three short resting cuffs decreased the within-subjects CV compared with the single cuff (CV=16% vs. 20%; for the average of three measurements and a single measurement, respectively). This suggests that averaging three short arterial occlusions for the measurement of resting oxygen consumption produces a modest reduction in the variability. No evidence for short repeated cuffs influencing resting metabolic rate was observed.

Figure 9B:
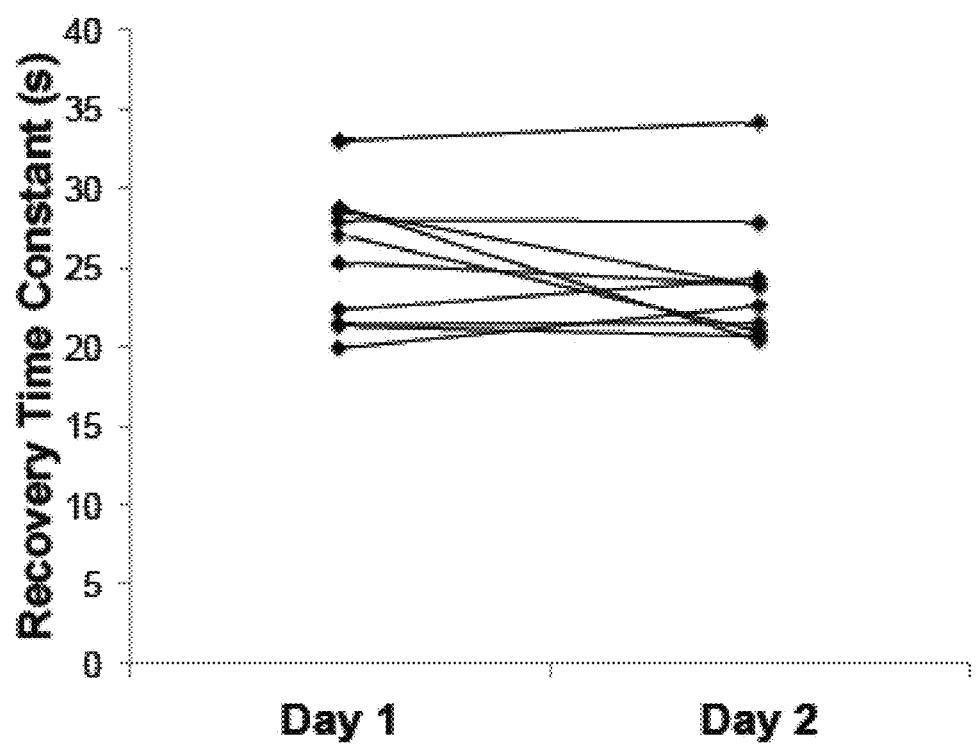
Figure 10:
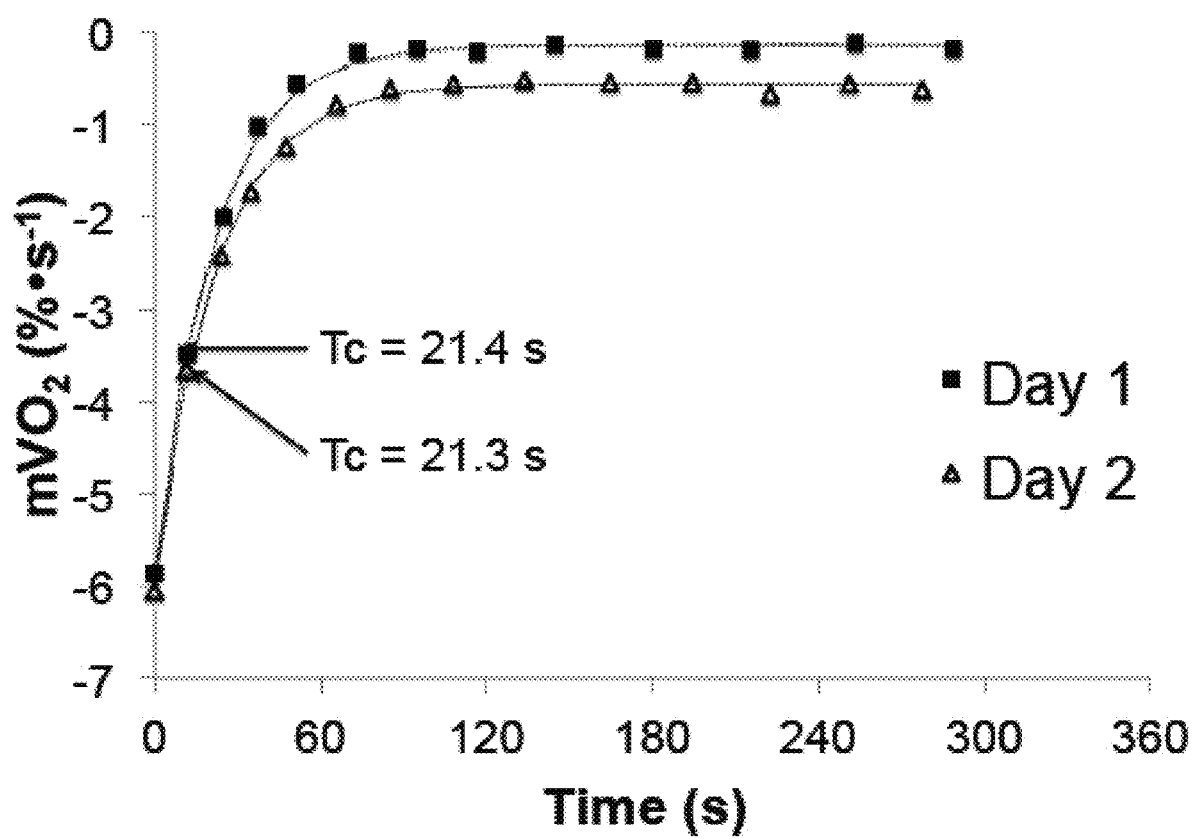
FIG. 10 is a graph that plots sample recovery curves for a healthy, able-bodied subject from Day 1 and Day 2. Raw blood-volume-corrected data are represented by solid-squares (Day 1) and open-triangles (Day 2).

End-exercise recovery of mVO₂ was measured by NIRS using brief (5-10 s) repeated arterial occlusions (~270 mmHg). The time constant for the recovery of mVO₂ following electrical stimulation was 24.5±4.0 seconds (CV=16%) for Day 1 and 22.1±2.1 seconds (CV=10%) for Day 2. Recovery mVO₂ time constants of all participants from Day 1 and Day 2 is shown in FIG. 9B. Representative mVO₂ recovery curves from a single subject for Day 1 and Day 2 are shown in FIG. 10. The mean coefficient of variation between Day 1 and Day 2 was 10.6% (Table 2).

Figure 11A:
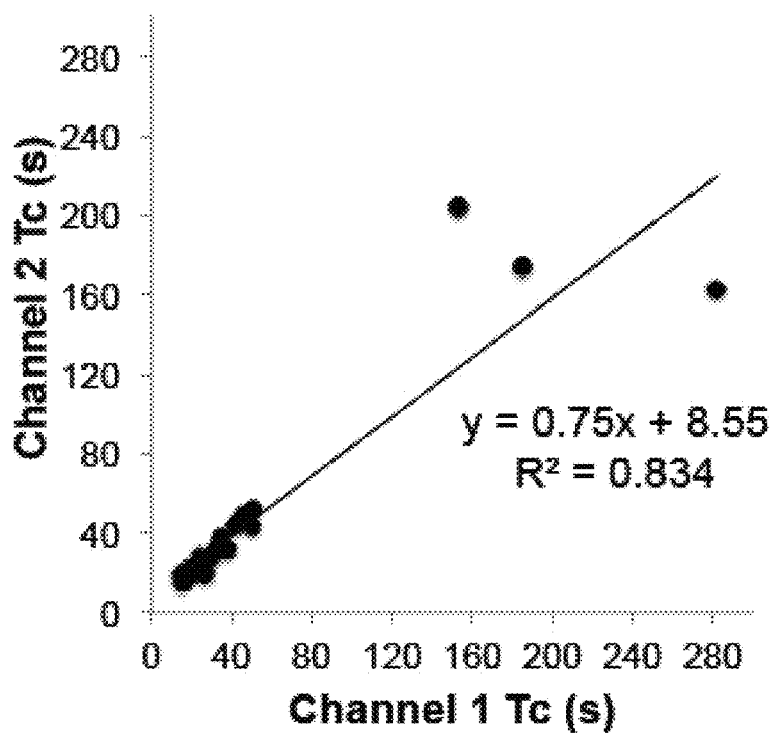
FIGS. 11A and 11B comprises graphs that show comparisons between the NIRS inter-optode distances for blood-volume-corrected recovery time constants.
Figure 11B:
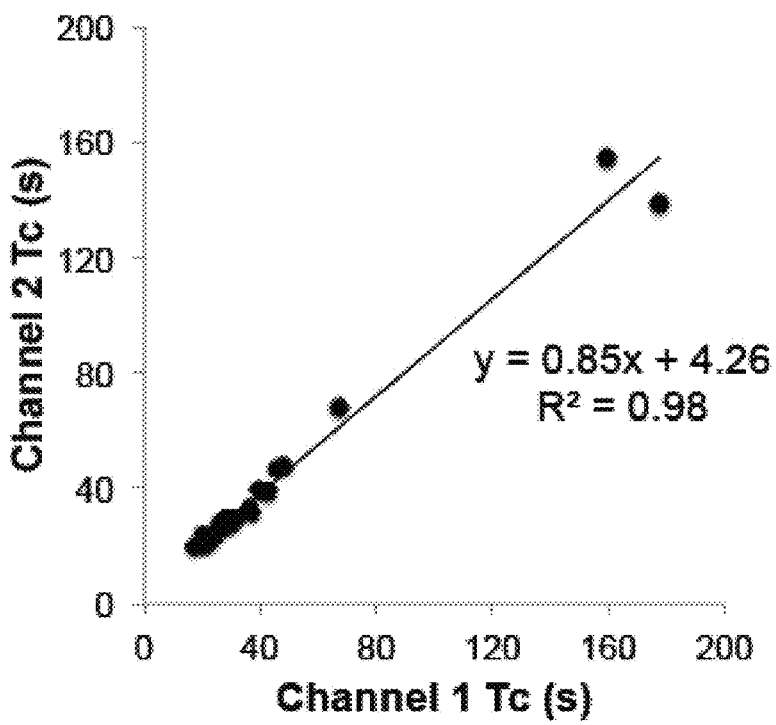

All NIRS testing was performed using two inter-optode distances ranging from 3-4.5 cm. The resting mVO₂ measured at the shallow versus deep NIRS signals were compared and good agreement was observed between channels (r=0.91, p<0.001) only when values were expressed as a percentage of the ischemic calibration. Using a differential pathlength factor (DPF) of 4, as recommended by the manufacturer, the relationship between shallow and deep penetration depths is weaker but still significant (r=0.68, p<0.001). FIG. 11 illustrates the agreement between penetration depths for the corrected recovery time constants. There were no significant differences in mVO₂ between penetration depths (p=0.21).

Figure 12A:
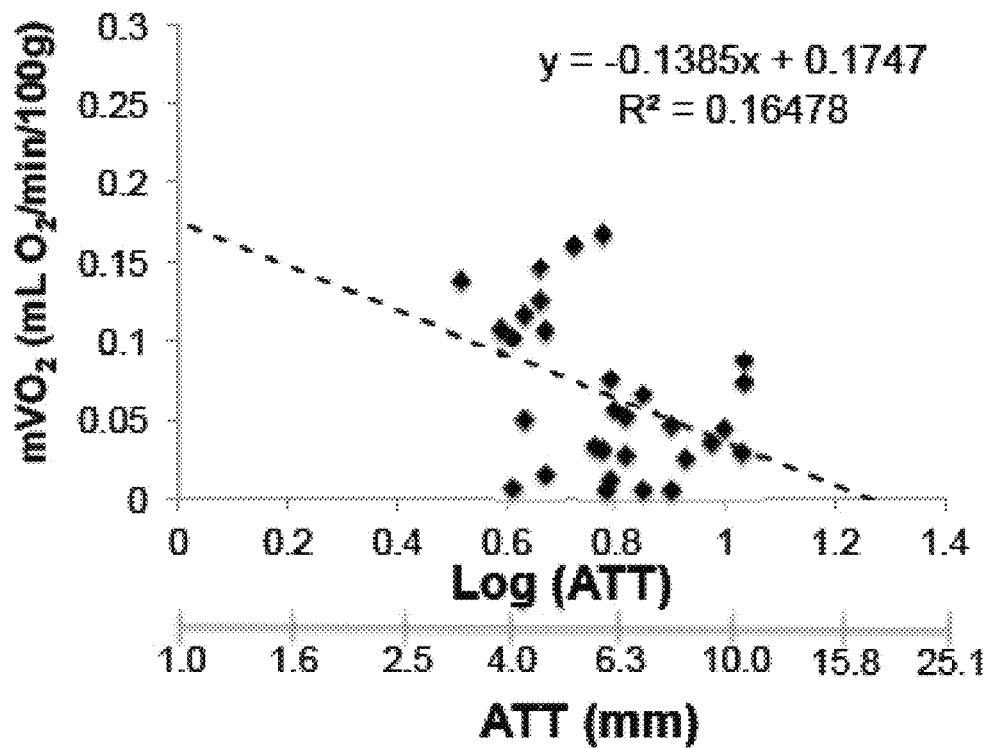
FIGS. 12A and 12B comprises graphs that illustrate the relationship between resting muscle oxygen consumption and adipose tissue thickness. (A) Calculation of resting $mVO_2$ in absolute units using a DPF=4. (B) Calculation of $mVO_2$ as a percentage of the ischemic calibration.
Figure 12B:
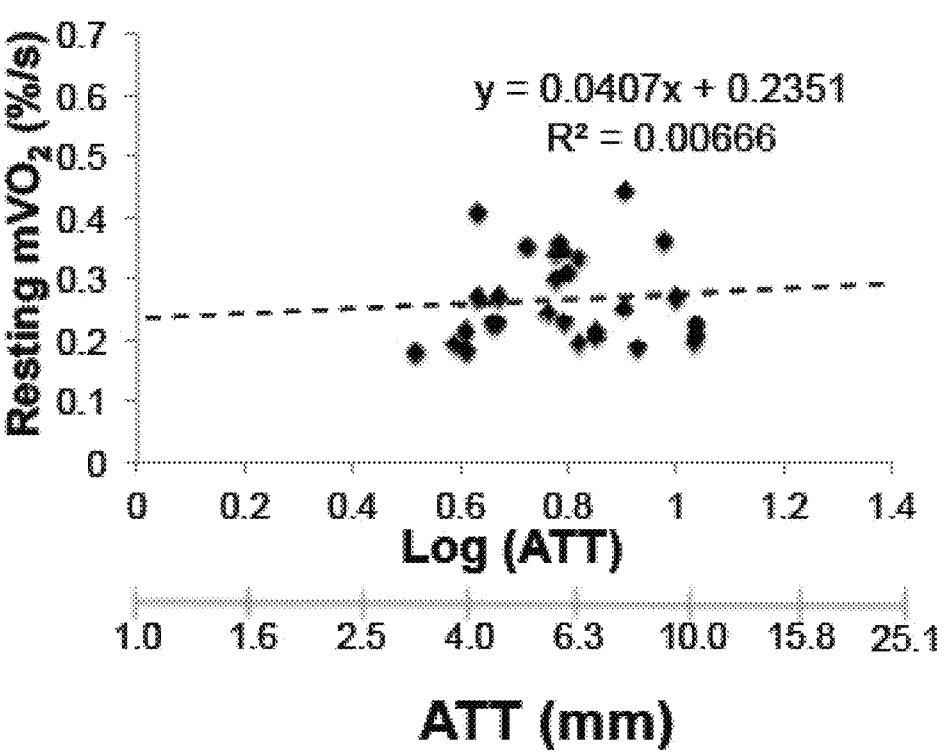

Adipose tissue thickness (ATT) was 6.0±1.6 mm on top of the medial gastrocnemius and 8.0±2.8 mm on top of the vastus lateralis muscle. ATT ranged from 3.3 mm to 12.0 mm in our participants. Resting mVO₂ was expressed two ways: using the recommended DPF of 4 to calculate absolute concentration changes and as a percentage of the ischemic calibration. The influence of ATT on mVO₂ for both methods is shown in FIG. 12. There was a significant relationship between ATT and mVO₂ (r=0.41, p=0.026) calculated using the DPF method (FIG. 12A). This relationship was no longer existent (r=0.006, p=0.668) when expressing resting mVO₂ as a percentage of the ischemic calibration (FIG. 12B).

Discussion of Findings

A primary finding of the study was the demonstration of methods to correct NIRS signals to account for changes in blood volume. The three different methods of blood volume correction resulted in consistent and reliable NIRS-based signals of skeletal muscle O₂Hb and HHb signals during arterial occlusion measurements of oxidative metabolism. The appearance of blood volume changes in the NIRS signal, even with arterial and venous occlusion, has been reported by others. The data from the raw, uncorrected signals support these volume effects. The data also support the idea that the HHB signal is less susceptible to changes in blood volume. While less influenced by blood volume shifts with occlusion, the uncorrected HHb signal resulted in recovery time constants that were twice as variable when compared with the blood volume corrected HHb time constants. This suggests that the blood volume correction is needed to accurately detect oxygen consumption measurements for all the signals coming from the NIRS devices. The cause of blood volume changes during arterial occlusions is currently unknown. Blood volume changes could be attributed to movement of heme concentrations from larger vessels (undetectable by NIRS) to microvascular beds detected by NIRS. In most cases seen in this study, the proportion of heme was primarily oxygenated heme, suggesting the influx of detectable signal was coming from the arterial side of the vascular tree. Because the correction factor to account for blood volume was not consistent between participants and test sessions, it appears that the correction method needs to be applied to each set of experiments.

In the study, resting oxygen consumption was more variable than the post-exercise recovery of oxygen consumption. The variability of resting measurements of muscle metabolism in this study was consistent with previous studies.

Evidence was provided supporting that the NIRS measurements for the recovery rate of mVO₂ after electrical stimulation exhibit good reliability. A mean coefficient of variation of 10% (range 1-22%) between Day 1 and Day 2 was observed. The results are comparable to coefficients of variation reported for phosphocreatine recovery kinetics. The time constant for recovery of mVO₂ measured in the gastrocnemius muscle also agrees with some reported values for phosphocreatine recovery, but is faster than other reports. One possible explanation for this difference is the individuals included in the reproducibility portion of this study were aerobically conditioned. Endurance trained individuals have faster phosphocreatine recovery rates when compared to their sedentary or less aerobically fit counterparts.

There are a number of potentially confounding factors for the quantification of continuous wave NIRS signals including unknown optical pathlength, absorption, and scattering coefficients, as well as the influence of adipose tissue thickness. The development of frequency- and time-domain NIRS devices has enabled the continuous measurement of the pathlength and absorption/scattering coefficients. However, the influence of ATT on NIRS signals still exists even with more advanced NIRS devices. In the case of this study, adipose tissue thickness will influence the NIRS signal as the estimated depth of penetration is one half the inter-optode distance. The differential pathlength factor (DPF), which corrects for the scattering of photons in tissue, has been applied to CW-NIRS for calculation of absolute concentration changes. With the large range of adipose tissue thickness (3.3-12.0 mm) we found a significant relationship between $mVO_2$ calculated using the DPF method and ATT (FIG. 12A). The results are consistent with previous studies. With the application of an ischemic calibration, the $mVO_2$ expressed as a percentage was no longer influenced by ATT (FIG. 12B). Thus, the results support the use of a physiological ischemic calibration for the calculation of muscle oxygen saturation and consumption.

The study used two inter-optode separation distances. This enabled comparison of measurements of muscle oxygen consumption between inter-optode distances in order to account for the potential effect of penetration depth on the metabolic measurements. The depth of muscle activation with electrical stimulation was unknown in this study, which could mean that some inactive tissue is contributing to NIRS signals. No significant influence of optode distance (sample depth) on muscle metabolic measurements was observed, suggesting that the measurements of mitochondrial function can be compared between people with different ATT thicknesses and intramuscular fat percentages, as long as an ischemic calibration is performed.

In this study, the calculation of $mVO_2$ in absolute units was influenced by adipose tissue and skin overlying the muscle. Therefore, an ischemic calibration was chosen to report the measurements of $mVO_2$ as a percentage change per unit time. This was a limitation in the study. To convert these relative units to absolute units of oxygen consumption (mM $O_2$), assumptions would need to be made regarding muscle hematocrit, myoglobin concentration, and the contribution of myoglobin/hemoglobin to the NIRS signals.

In a further study, it was confirmed that NIRS measurements of mitochondrial function were comparable for voluntary and electrical stimulation exercises. Moreover, it was confirmed that the intensity of the exercise does not influence the measurement of the recovery of $mVO_2$. The recovery of $mVO_2$ after low- to moderate-intensity exercise appears to follow a monoexponential function, and measurements can be made with reasonably small increases in $mVO_2$.

In conclusion, mitochondrial capacity was measured using NIRS and assessed the reliability and reproducibility of resting muscle oxygen consumption and the recovery rate of muscle oxygen consumption after exercise. A blood volume correction has been developed and applied to arterial occlusion measurements of oxygen consumption. Without correcting for blood volume changes, the metabolic exchange between $O_2Hb$ and HHb is unreliable.

The invention claimed is:

1. A method for measuring mitochondrial capacity, the method comprising:
    applying an occlusion device to a limb of a patient;
    applying a sensor and at least one electrode of a near-infrared spectroscopy (NIRS) device to the limb at a point distal of the occlusion device;
    performing one or more arterial occlusions on the patient's limb by constricting blood flow through the patient's arteries with the occlusion device;
    measuring with the near-infrared spectroscopy device oxygenated hemoglobin/myoglobin and deoxygenated hemoglobin/myoglobin within the patient's limb during the occlusions;
    receiving with a computing device in communication with the near-infrared spectroscopy device measurements of the oxygenated hemoglobin/myoglobin and deoxygenated hemoglobin/myoglobin measured by the near-infrared spectroscopy device, the computing device comprising a processor and memory that stores instructions for determining mitochondrial capacity;
    calculating with the computing device a blood volume correction factor that accounts for a change in blood volume that occurs during the arterial occlusions; and
    applying with the computing device the correction factor to the measured oxygenated hemoglobin/myoglobin and deoxygenated hemoglobin/myoglobin measurements to compute corrected oxygenated hemoglobin/myoglobin and deoxygenated hemoglobin/myoglobin measurements.

2. The method of claim 1, wherein applying an occlusion device comprises applying a blood pressure cuff to the patient's limb.

3. The method of claim 1, wherein calculating a blood volume correction factor comprises the computing device calculating a correction factor that adjusts the measured oxygenated hemoglobin/myoglobin and deoxygenated hemoglobin/myoglobin signals so that a decrease in the oxygenated hemoglobin/myoglobin signal is equivalent to an increase in the deoxygenated hemoglobin/myoglobin signal.

4. The method of claim 1, wherein the blood volume correction factor is calculated by the computing device using the following equation:

$$\beta_i = \frac{|O_2Hb_i|}{(|O_2Hb_i| + |HHb_i|)}$$

where $\beta$ is the blood volume correction factor, $O_2Hb$ is the oxygenated hemoglobin/myoglobin signal, and HHb is the deoxygenated hemoglobin/myoglobin signal.

5. The method of claim 4, wherein applying the correction factor comprises the computing device calculating corrected oxygenated hemoglobin/myoglobin and deoxygenated hemoglobin/myoglobin signals using the following equations:

$$O_2Hb_c = O_2Hb - [tHb*(1-\beta)]$$

$$HHb_c = HHb - (tHb*\beta)$$

where $O_2Hb_c$ is the corrected oxygenated signal, $HHb_c$ is the corrected deoxygenated hemoglobin/myoglobin signal, and tHb is the arithmetic sum of $O_2Hb$ and HHb.

6. The method of claim 1, wherein calculating a blood volume correction factor comprises the computing device determining blood volume change during one or more resting occlusions and using the blood volume change to calculate a global correction factor that will be applied to all measured signals.

7. The method of claim 1, wherein calculating a blood volume correction factor comprises the computing device determining blood volume change during each arterial occlusion and using the blood volume changes to calculate separate correction factors that will be individually applied to the signals measured for each occlusion.

8. The method of claim 1, wherein calculating a blood volume correction factor comprises the computing device iteratively searching for a blood volume correction factor that results in the smallest error for the difference between the measured signals.

9. The method of claim 8, wherein iteratively searching for the blood volume factor comprises the computing device applying a Nelder-Mead algorithm.

10. The method of claim 9, wherein applying the Nelder-Mead algorithm comprises the computing device searching for a correction factor that results in the smallest least squares difference between curves for the oxygenated hemoglobin/myoglobin and deoxygenated hemoglobin/myoglobin signals.

11. The method of claim 1, further comprising calculating with the computing device oxygen consumption for each occlusion using the corrected oxygenated hemoglobin/myoglobin and deoxygenated hemoglobin/myoglobin measurements to obtain oxygen consumption data.

12. The method of claim 11, further comprising fitting the oxygen consumption data to an exponential curve to obtain a representation of mitochondrial function using the computing device.

* * * * *